United States Patent [19]
Chen et al.

[11] Patent Number: 6,138,681
[45] Date of Patent: *Oct. 31, 2000

[54] ALIGNMENT OF EXTERNAL MEDICAL DEVICE RELATIVE TO IMPLANTED MEDICAL DEVICE

[75] Inventors: James C. Chen, Bellevue; Brian D. Wilkerson, Issaquah; Darrin Huston, Enumclaw, all of Wash.

[73] Assignee: Light Sciences Limited Partnership, Issaquah, Wash.

[*] Notice: This patent issued on a continued prosecution application filed under 37 CFR 1.53(d), and is subject to the twenty year patent term provisions of 35 U.S.C. 154(a)(2).

[21] Appl. No.: 08/949,308

[22] Filed: Oct. 13, 1997

[51] Int. Cl.$^7$ ................................................. A61B 19/00
[52] U.S. Cl. ............................ 128/899; 128/897; 128/99; 128/653.1; 607/156
[58] Field of Search ........................... 128/897.99, 653.1; 607/156

[56] References Cited

U.S. PATENT DOCUMENTS

| | | | |
|---|---|---|---|
| 5,005,592 | 4/1991 | Cartmell | 128/899 |
| 5,099,845 | 3/1992 | Besz et al. | 128/653.1 |
| 5,425,382 | 6/1995 | Golden et al. | 128/899 |
| 5,645,065 | 7/1997 | Shapiro et al. | 128/899 |
| 5,727,552 | 3/1998 | Ryan | 128/899 |

FOREIGN PATENT DOCUMENTS 0399536  11/1990  European Pat. Off. ............... 128/899

OTHER PUBLICATIONS

Webster's II New Riverside University Dictionary, p. 715, 1984.

*Primary Examiner*—John P. Lacyk
*Attorney, Agent, or Firm*—Ronald M. Anderson

[57] ABSTRACT

The alignment and positioning of an external device relative to an internal device is indicated on a display and/or by an acoustical signal. In the disclosed application, the external device transcutaneously transmits electromagnetic energy to an internal receiver to provide electrical power for an implanted medical device. To ensure optimal coupling between the external transmitter and the internal receiver, two permanent magnets are disposed at spaced-apart positions on the internal receiver. The magnetic field strength of the permanent magnets is sensed by a pair of correspondingly spaced-apart Hall effect sensor on the external transmitter. As the external transmitter is moved about over the internal receiver, the signals produced by the Hall effect sensors drive a display of light emitting diodes (LEDs) that indicates when the maximum magnetic field strength is achieved, i.e., when the Hall effect sensors on the external transmitter are each positioned directly opposite the corresponding permanent magnets on the internal receiver.

46 Claims, 7 Drawing Sheets

ALIGNMENT OF EXTERNAL MEDICAL DEVICE RELATIVE TO IMPLANTED MEDICAL DEVICE

FIELD OF THE INVENTION

This invention generally relates to the alignment of an external medical device with an internal medical device separated by a tissue layer of a patient's body, and more specifically, to determining the alignment of an external transmitter and an internal receiver employed to transfer electromagnetic energy transcutaneously.

BACKGROUND OF THE INVENTION

Transcutaneous transmission of energy from an external transmitter to an internal receiver is known in the prior art. Pacemakers and other types of medical devices that are implanted and require electrical energy from a battery to operate typically rely upon this type of system for recharging the battery. Although the external transmitter may be coupled to the internal receiver by a radio frequency signal, lower frequency electromagnetic coupling is generally more efficient.

To energize an implanted medical device with electromagnetically coupled power, an external transmitter coil comprising a plurality of coils of a conductor wound on a core is energized by a source of alternating electrical current. The flow of electrical current in the external transmitter coil induces a corresponding electrical current in the windings of an internal receiver coil. This electrical current can be applied to recharge the battery used by a device, or alternatively, can be employed to directly energize the implanted medical device.

Optimum transcutaneous energy transfer efficiency is achieved when the external transmitter coil is disposed on the surface of a patient's skin, directly opposite the internal receiver coil, with a minimum separation distance between the external transmitter and internal receiver coils. Depending upon the design of the external transmitter and internal receiver coils, several other factors can adversely affect the efficiency of their transcutaneous electromagnetic coupling. If the external transmitter and internal receiver coils are wound on cores, a misalignment of the pole faces of the external transmitter and internal receiver coils will reduce the coupling efficiency. Ideally, the axes of the internal receiver and the external transmitter coils should be aligned, so that electromagnetic field produced by the external transmitter coil will be concentrated in the core of the receiving coil. Any misalignment of the axes will reduce the efficiency with which energy is transferred between the two coils. However, since the internal receiver coil is inside the dermal layer of the patient's body, it is not visible. Furthermore, the internal receiver coil can shift relative to its original implanted location, so that any dye markings applied to the skin of the patient to show the original location of the internal receiver coil may become inaccurate and fail to properly indicate the position in which the external transmitter coil should be applied.

In the prior art, several techniques not relying upon external markings have been employed to ensure the proper positioning of an external transmitter coil relative to an internal receiver coil, for coils wound on pot-type cores. One technique uses an external transmitter pot core that is concave in shape, and an internal receiver pot core that has a convex shape. The convex shape of the internal receiver core disposed beneath a patient's skin creates a small bump on the epidermis. The external transmitter coil is placed over the bump and its concave shape enables it to be positioned to fit the contours of the convex bump produced by the internal receiver coil core. In this way, the external transmitter and internal receiver coils are positioned directly opposite each other so that efficient transfer of electrical power may occur.

Another technique used in the prior art employs rare earth magnets to position and support a cochlear implant. ("The Use of Rare-Earth Magnet Couplers in Cochlear Implants," K. Dormer et al., *The Laryngoscope*, Vol. 91, November 1981.) In this case, a cochlear stimulus signal is magnetically induced in the cochlear implant from an external coil. To support the external transmitter coil in alignment with the receiving coil of the implant, a $SmCo_5$ disc is encapsulated in the stem of a pot core used for the internal receiver coil, and a similar $SmCo_5$ disc of opposite magnetic polarity is included on the stem of the pot core of the external transmitter coil. The magnetic attraction between the rare earth magnetic discs tend to support and position the external transmitter coil opposite the internal receiver coil of the implant. However, this technique does not align the two coils other than along their central axes. The technique would thus not be applicable for aligning the pole faces of an external transmitter and an internal receiver having C-shaped cores, unless a pair of the rare earth magnets were used in both the external transmitter and internal receiver coils.

None of the prior art techniques enable a person to easily determine in real time the relative separation distance and alignment of the external transmitter and internal receiver coils. Significantly, frequent repositioning of the external transmitter coil may be required when an implanted medical device is energized directly by an induced electromagnetic current. A long felt need in the medical industry therefore exists for a system to indicate the position of an external transmitter coil relative to an internal receiver coil, so that a medical practitioner/patient can determine where to position the external transmitter coil to achieve optimal electromagnetic coupling to an internal receiver coil.

SUMMARY OF THE INVENTION

In accord with the present invention, apparatus is defined for determining a position and alignment of an external device relative to an implanted device, where the implanted device is separated from the external device by tissue. By determining their relative dispositions, the external device can be aligned with the implanted device. The apparatus includes two magnets that are disposed in the implanted device at spaced-apart locations. Two magnetic field sensors are disposed in the external device at spaced-apart locations generally corresponding to the spaced-apart locations of the magnets on the implanted device. The magnetic sensors each produce an electrical signal indicative of magnetic field strength. An indicator is coupled to the magnetic field sensors to receive the signals, and in response thereto, produces an indication of the magnetic field produced by the magnets, and thus an indication of a position and orientation of the external device relative to the implanted device. The indication enables the external device to be moved to a position that is opposite to and aligned with the implanted device, or alternatively, to a desired position relative to the implanted device.

In one embodiment, the indicator comprises a plurality of light sources arranged in an array. At least one of the light sources is energized to indicate a relative alignment of one of the magnets with one of the magnetic field sensors.

Similarly, at least another of the light sources is energized to indicate a relative alignment of the other of the magnets with the other of the magnetic field sensors.

In this embodiment, the plurality of light sources are preferably arranged side by side, forming a first section and a second section. One light source is energized in the first section, and another light source is energized in the second section. The disposition of each of the light sources energized in the first and second sections indicates the relative magnetic field strengths.

The magnetic field sensors each preferably comprise either a Hall effect sensor or a magneto resistive sensor. The magnets are preferably oriented so that their poles are in the same direction or alternatively, in the opposite direction.

In one embodiment, the indicator is an audible signal having at least two distinguishable characteristics. One characteristic varies with the alignment of one of the magnets relative to one of the magnetic field sensors, and the other characteristic varies with alignment of the other magnet relative to the other magnetic field sensor.

Another aspect of the present invention is directed to a method for determining a position of an external device in relation to an implanted device that is disposed within a patient's body and separated from the external device by tissue. The method includes steps that are generally consistent with the functions of the elements of the apparatus discussed above.

Yet another aspect of the present invention are directed at a method and apparatus for determining a separation between an external device and an implanted device. The distance between the two devices is indicated as a function of the signal produced by one or more field strength sensors disposed on either the external device or the implanted device, in response to the magnetic field produced by one or more magnets disposed on either device.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

Figure 8:
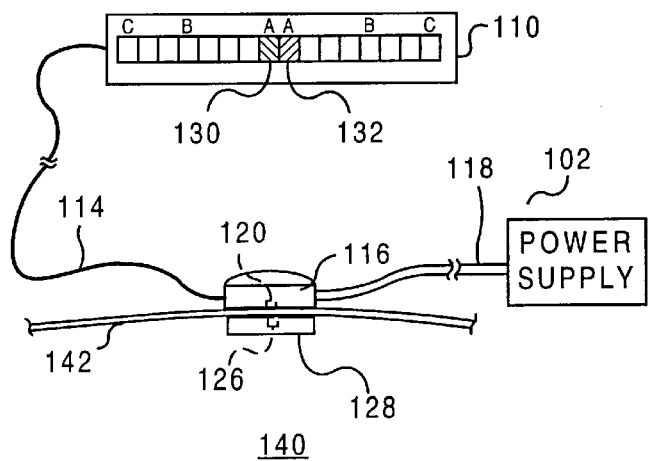
Figure 7A:
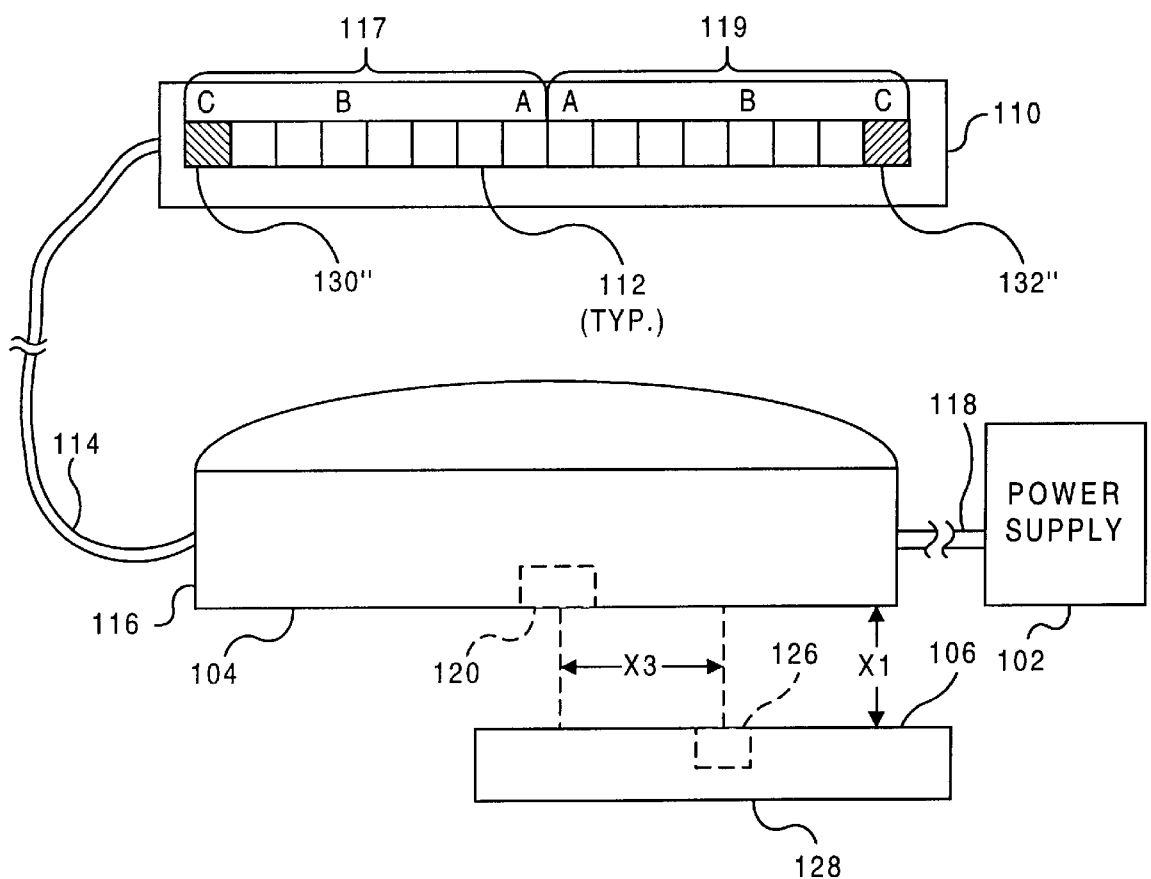
FIG. 7A is a side view of the external transmitter disposed over the internal receiver, but offset along the internal receiver's longitudinal axis.
Figure 7B:
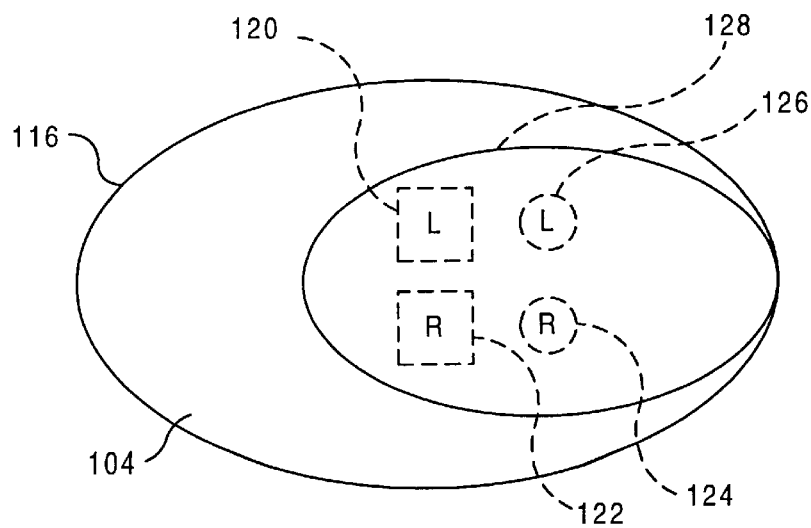

FIG. 7B is a bottom view of the external transmitter disposed over the internal receiver, the pair of magnets disposed on the bottom surface of the internal receiver being offset longitudinally relative to the pair of Hall effect sensors on the external transmitter; and FIG. 8 is a side elevational view of the external transmitter disposed over the internal receiver implanted within a patient's chest.

DESCRIPTION OF THE PREFERRED EMBODIMENT

Figure 1:
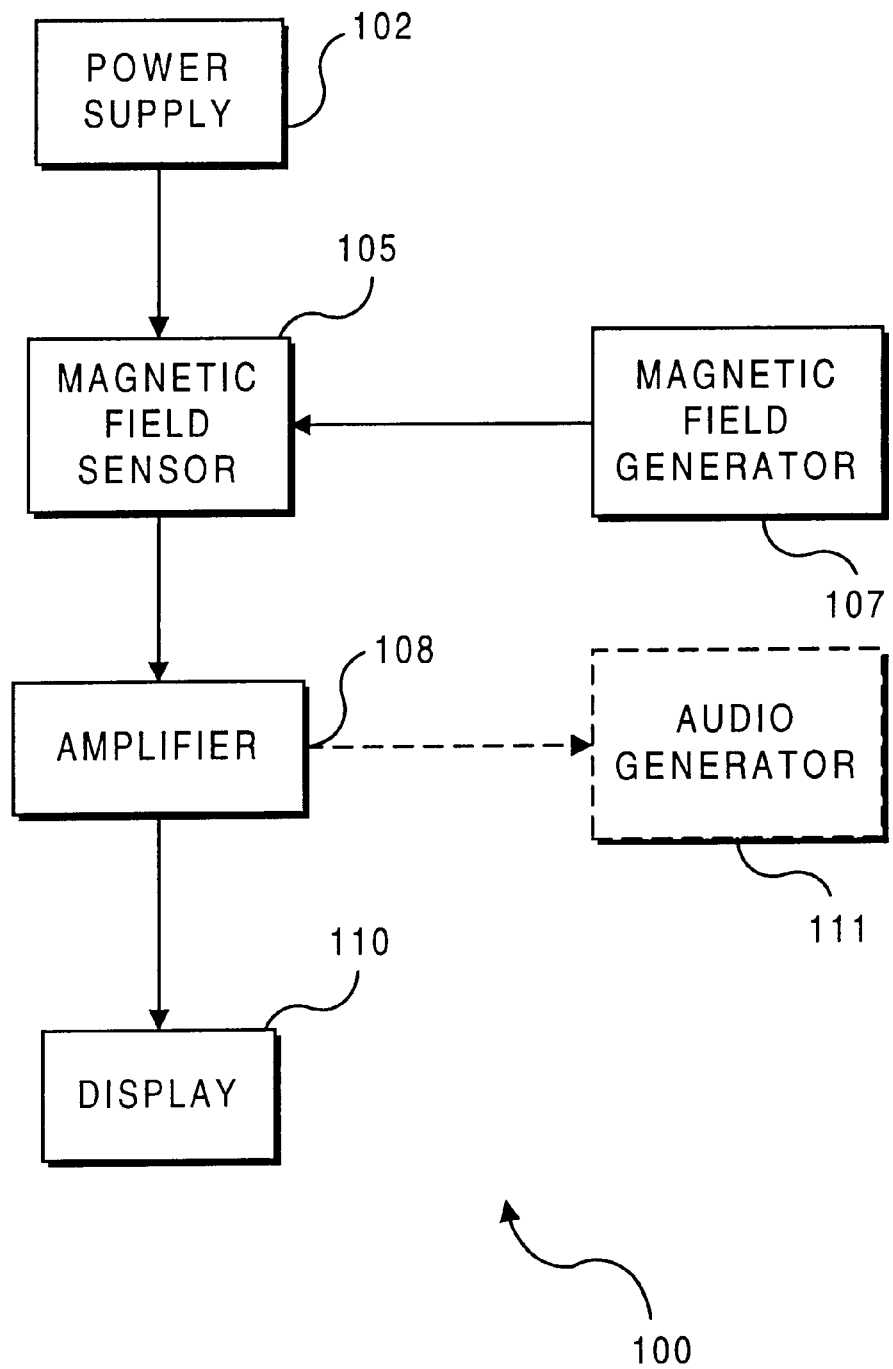
FIG. 1 is a functional block diagram of a system for determining the position and orientation of an external transmitter relative to an internal receiver used for transcutaneous energy transmission.

In FIG. 1, a system 100 for determining the position and orientation of one object relative to another is shown. A power supply 102 is coupled to a magnetic field sensor 105. The magnetic field sensor produces an output signal indicative of the strength and direction of a magnetic field that is produced by a magnetic field generator 107. The signal produced by magnetic field sensor 105 is input to an amplifier 108, which produces an amplified signal for driving a display 110. The display provides an indication of the separation distance (or relative disposition), and the alignment or orientation of magnetic field generator 107 relative to the magnetic field sensor 105. An audio generator 111 is optionally coupled to amplifier 108, so that an audible indication of the separation distance and alignment may be provided. Various characteristics of an audio signal, such as the amplitude, phase, and frequency can be controlled in response to the signal output from amplifier 108 as an indicator of the relative position and orientation of the magnetic field generator and magnetic field sensor. It is contemplated that audio generator 111 may be employed instead of display 110, or in combination with the display.

Although other types of magnetic field sensors such as eddy current sensors can be used, a preferred embodiment of the present invention employs a Hall effect sensor. However, it is also contemplated that a magneto resistive sensor is a good choice for this purpose. The signal produced by a Hall effect sensor is a transverse voltage differential that appears across opposite edges of a strip of conducting material in response to a magnetic field oriented perpendicular to a flow of an electrical current longitudinally through the strip and generally perpendicular (or at some non-zero angle) to the surface of the strip. The polarity of the voltage potential depends upon the direction of the magnetic field and the direction of the electrical current flowing through the strip. The force exerted by the magnetic field causes the flowing electrons to migrate towards one edge of the strip in accord with the "right hand rule," i.e., as defined by the cross product of the magnetic field and electrical current vectors, $\vec{B} \times \vec{I}$.

Magnetic fields can be produced using either an electromagnet or a permanent magnet. An electromagnet must be energized with an electrical current supplied by a power source that is electrically coupled to a winding. In contrast, a permanent magnet provides a constant magnetic field and need not be coupled to a power supply, since it does not require any electrical current. In the present preferred embodiment, it is generally less desirable to produce a magnetic field with an electromagnet, because the electromagnet will preferably be disposed at a site within a patient's body, and a storage battery or other source of electrical current disposed within the patient's body that would be used to energize the electromagnet is better utilized for other purposes.

A permanent magnetic material has been developed, which generates a magnetic field five to ten times greater than a conventional alnico permanent magnet per unit of weight. These magnets are fabricated of rare earth metals, such as neodymium, and they can be manufactured in a wide variety of shapes. Additionally, rare earth magnets can have physical dimensions smaller than an electromagnet or conventional alnico magnet that produces an equivalent magnetic field strength. Consequently, super neodymium (or other rare earth) permanent magnets having biocompatible coatings are preferably employed as a source of a magnetic field, i.e., for magnetic field generator 107, in the present invention.

Figure 2A:
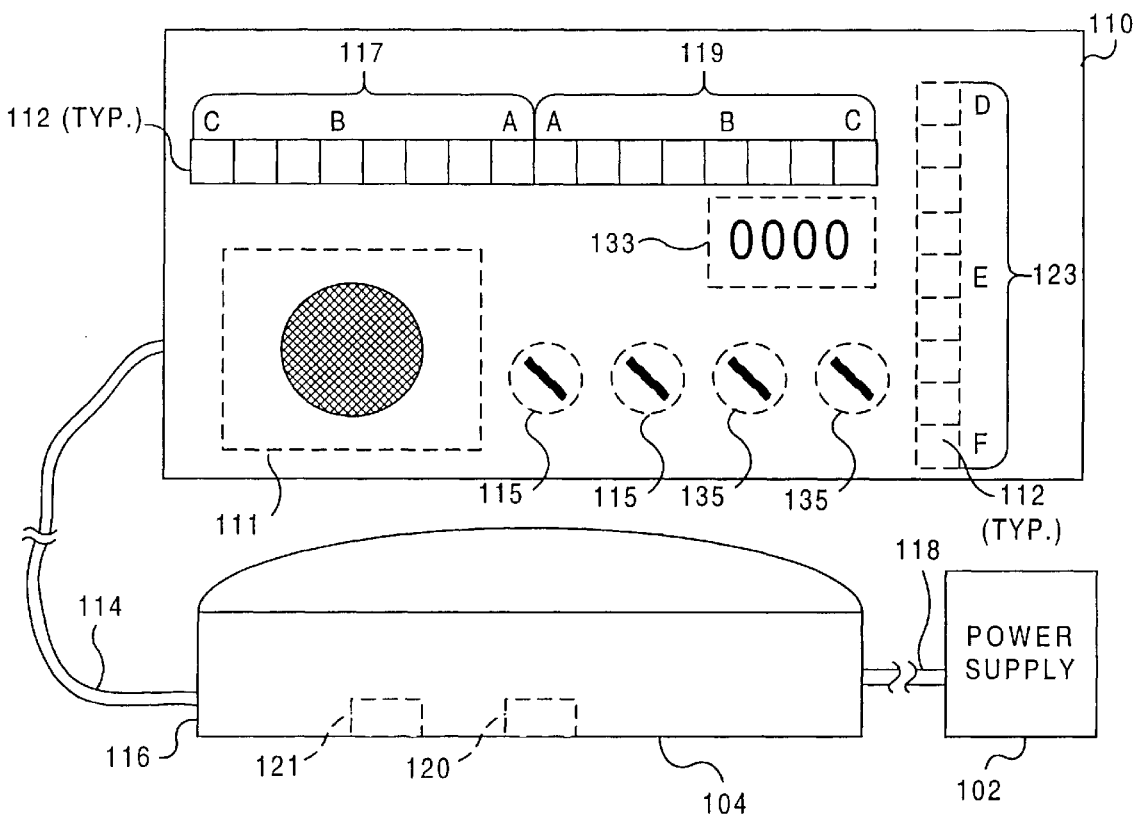
FIG. 2A is a side elevational view of the external transmitter and a display indicating its orientation and position relative to the internal receiver.
Figure 2B:
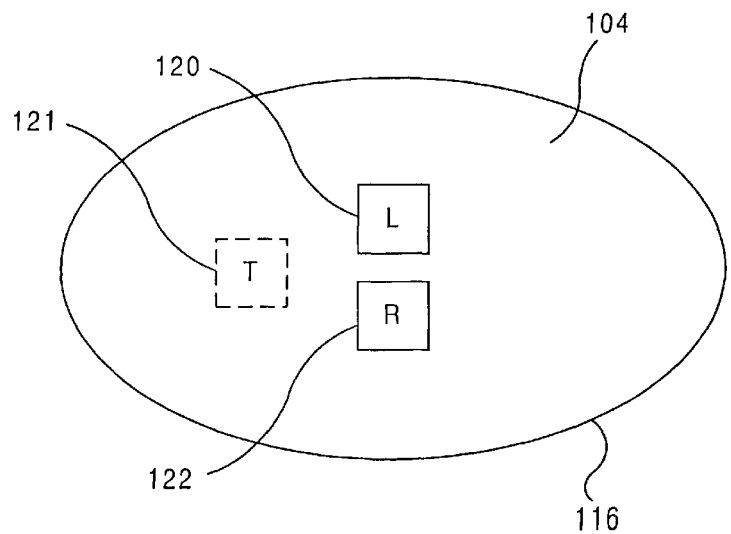
FIG. 2B is a bottom view of the external transmitter, showing a pair of Hall effect sensors disposed therein.
Figure 3A:
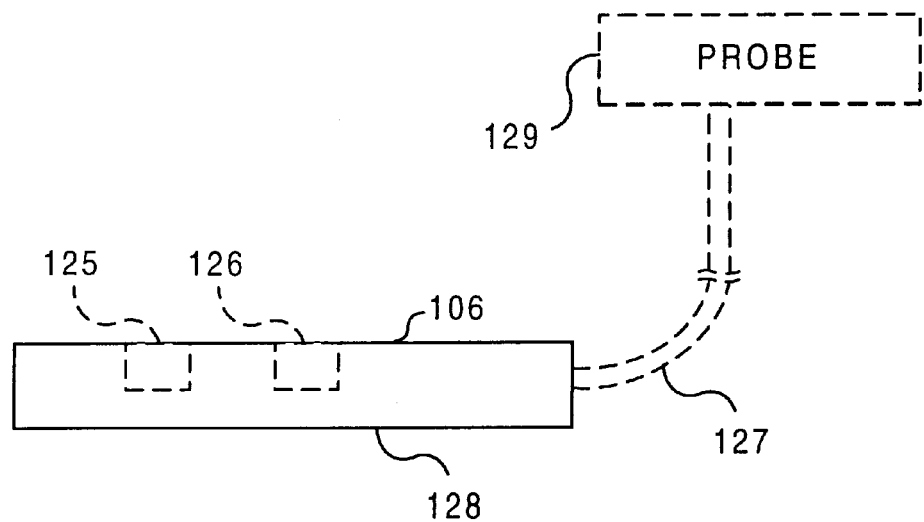
FIG. 3A is a side view of the internal receiver.
Figure 3B:
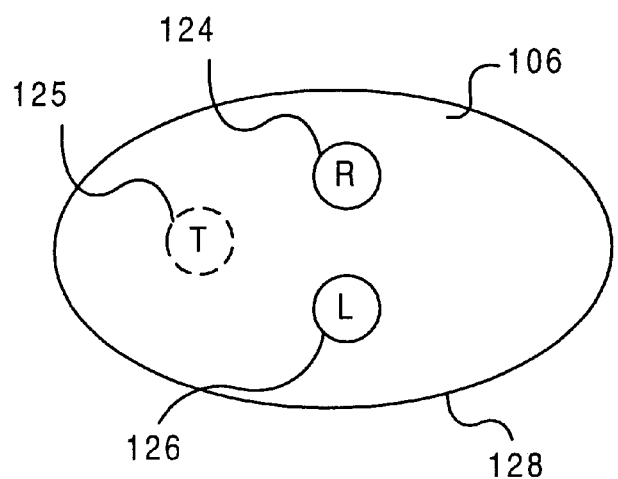
FIG. 3B is a top view of the internal receiver, showing a pair of permanent magnets disposed therein.

FIGS. 2A and 2B illustrate an external transmitter 116 that is used for transcutaneous energy transfer to an internal receiver 128 that is shown in FIGS. 3A and 3B. The external transmitter has a pair of spaced-apart Hall effect sensors 120 (left) and 122 (right) disposed in the middle transverse portion of a bottom surface 104 of the external transmitter. External transmitter 116 is electrically coupled by a lead 118 to power supply 102, and another lead 114 couples external transmitter 116 to display 110. It should be noted that power supply 102 is preferably included within the housing of display 110, so that leads 114 and 118 are together. The display includes a plurality of LEDs 112 disposed in an array along its longitudinal axis; pairs of LEDs 112, one in each of a left section 117 and a right section 119 are illuminated to indicate the magnetic field strength and thus, the position and alignment of external transmitter 116 relative to internal receiver 128, as explained below.

Audio generator 111 is optionally coupled to external transmitter 116 and a varying audio signal is used to indicate position and alignment of the external transmitter relative to internal receiver 128. Also, audio generator 111 may be employed to indicate an alarm when external transmitter 116 is moved away from an optimally aligned position relative to internal receiver 128. Further, audio generator 111 may be used to produce an audio "lock in" signal that indicates when external transmitter 116 is ideally aligned with the internal receiver. Additionally, a gage 133 is optionally coupled to external transmitter 116 to indicate the disposition of the external transmitter relative to the internal receiver. Gage 133 may use an analog and/or digital indication of position, alignment, and/or separation distance. Also, it is contemplated that gage 133 may optionally indicate parameters associated with a medical therapy applied by the internal receiver or by a probe 129, which is coupled to the internal receiver, such as temperature, energy consumption, and light output.

Also, a pair of range controls 115 (one for left section 117 and one for right section 119) are optionally disposed in display 110 for selecting one of a plurality of measurement ranges for the magnetic field strength indicated by the illumination of LEDs 112, and each. For example, selecting a "coarse" setting would provide a measurement range of zero to four centimeters, for indicating the distance between external transmitter 116 and the internal receiver, while a "fine" setting would provide a shorter measurement range of zero to two centimeters. Range controls 115 may also be coupled to an internal look up table (stored in an electronic memory—not shown) that correlates the strength of the magnetic field measured by the magnetic field sensors to the distance between the external transmitter and internal receiver 128, so that more precise resolution in the distance separating the external device from the internal receiver displayed on gage 133 is automatically provided in response to selection of the fine setting. In addition, a pair of zero offset controls 135 are included (one for each section of LEDs) so that the selected range can be offset from zero, e.g. to provide a range from two to four centimeters instead of from zero to two centimeters.

As will be evident from FIG. 2B, external transmitter 116 has an elliptically-shaped profile. Although not separately shown in FIGS. 2A and 2B, amplifier 108 may be disposed within external transmitter 116. Alternatively, the amplifier can be included within the enclosure for display 110.

Optionally, another (i.e., a third) Hall effect sensor 121 is disposed adjacent one end of external transmitter 116, along its longitudinal axis and proximate its bottom surface 104. Further, display 110 optionally includes a plurality of LEDs 112 disposed in an array 123. A single LED 112 in array 123 is illuminated in response to the signal produced by Hall effect sensor 121, to indicate the magnetic field strength at the sensor. As explained below, array 123 allows measurement of the tilt of external transmitter 116 relative to internal receiver 128. It should be noted that two magnetic field sensors can instead be mounted along the longitudinal axis, with a third mounted along the latitudinal axis, adjacent one edge of the bottom surface of the external transmitter; magnetic field generators would then be provided in corresponding positions on the internal receiver. This option is not illustrated, but will be readily apparent in view of the disclosed embodiment. Although two magnetic field generators and two corresponding Hall effect sensors can also indicate tilt relative to a single axis, the signals produced by the two Hall effect sensors would not enable the user to clearly distinguish between alignment errors and tilt errors. Three or more magnetic field generators and corresponding Hall effects sensor are preferable, since they remove this ambiguity and quantify the extent of any tilt error.

FIGS. 3A and 3B illustrate details of internal receiver 128, which is designed to be implanted within a patient's body to provide electrical current to recharge a battery or directly energize implanted probe 129 through a lead 127. Alternatively, internal receiver 128 may itself include electronic devices that provide medical therapy to a portion of the patient's body adjacent to the internal receiver. Rare earth permanent magnets 124 (right) and 126 (left) are disposed in the middle portion of an outwardly facing (top) surface 106 of the internal receiver (i.e., facing outward of the patient's body). Internal receiver 128 also has an elliptically-shaped profile. All of the exposed surfaces of internal receiver 128 and of the leads are made from or coated with a polymeric substance that is biologically inert, such as a TEFLON™ polymer or silicone. Optionally, assuming that hall effect sensor 121 is provided in external transmitter 116, another rare earth permanent magnet 125 is disposed adjacent an end of internal receiver 128, along its longitudinal axis and proximate outwardly facing (top) surface 106. Magnet 125 is thus disposed in the internal receiver at a position corresponding generally to that of Hall effect sensor 121 in the external transmitter and generates a magnetic field usable for determining the tilt of the external transmitter relative to the internal receiver.

Figure 4A:
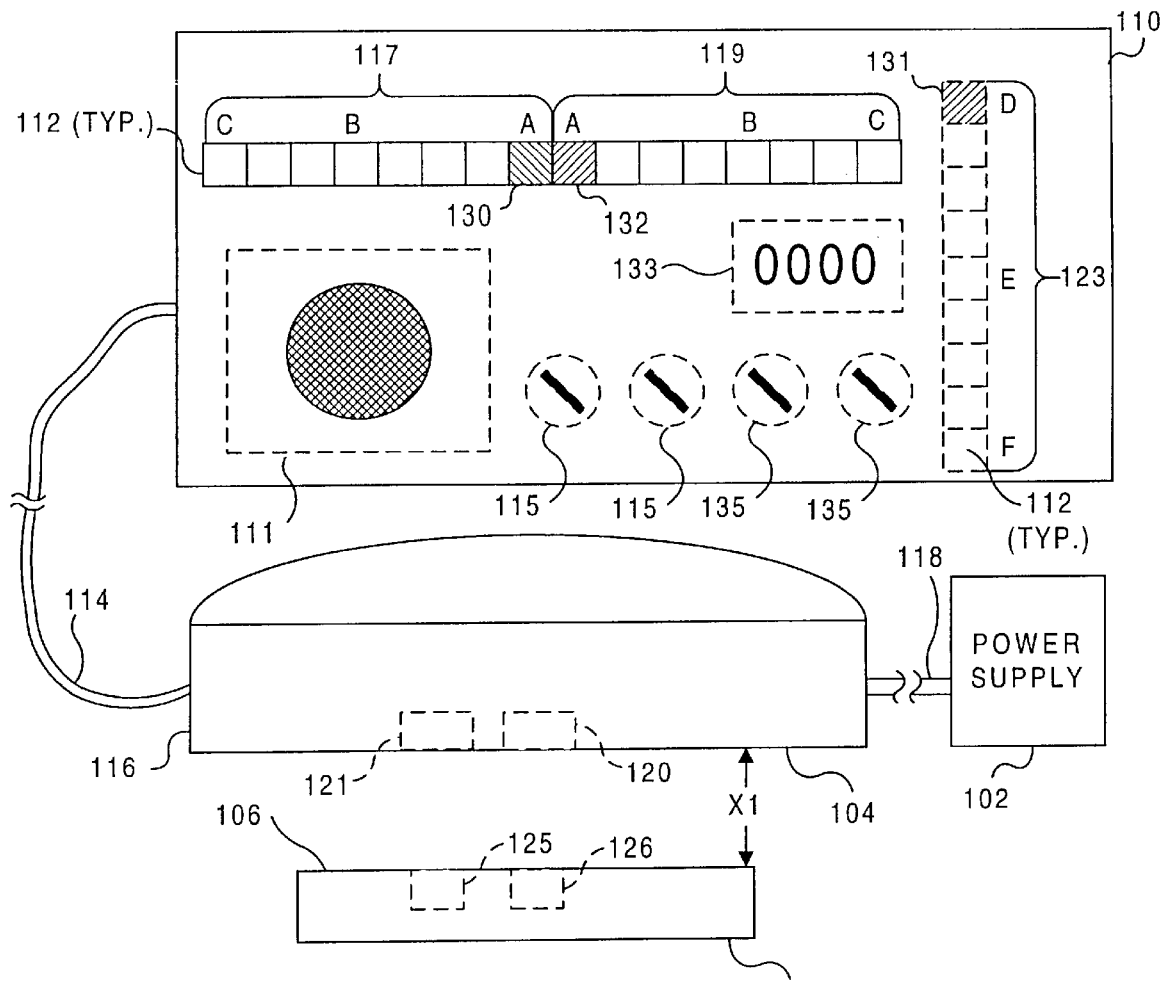
FIG. 4A is a side elevational view of the external transmitter disposed opposite the internal receiver, aligned at a desirable separation distance.

In FIG. 4A, external transmitter 116 is disposed over internal receiver 128 at a minimally anticipated separation distance (X1). This distance corresponds to the minimally anticipated thickness of the dermal layer (approximately 0.5 centimeters) that typically separates the internal receiver from the external transmitter. In this example, external transmitter 116 is coaxially disposed in alignment with internal receiver 128, so that Hall effect sensors 120 and 122 and permanent magnets 126 and 124 are respectively aligned opposite each other. Optional magnet 125 is also aligned with optional Hall effect sensor 121.

To indicate that the external transmitter is properly aligned and oriented relative to the internal receiver at least at the minimally desirable separation distance, an LED 130 at the right end of left section 117 and an LED 132 at the left end of right section 119 of display 110 are illuminated. The illumination of LED 130 and LED 132 indicates that external transmitter 116 is aligned with internal receiver 128 and that the distance between the external transmitter and the internal receiver is at least the minimal separation distance.

Figure 4B:
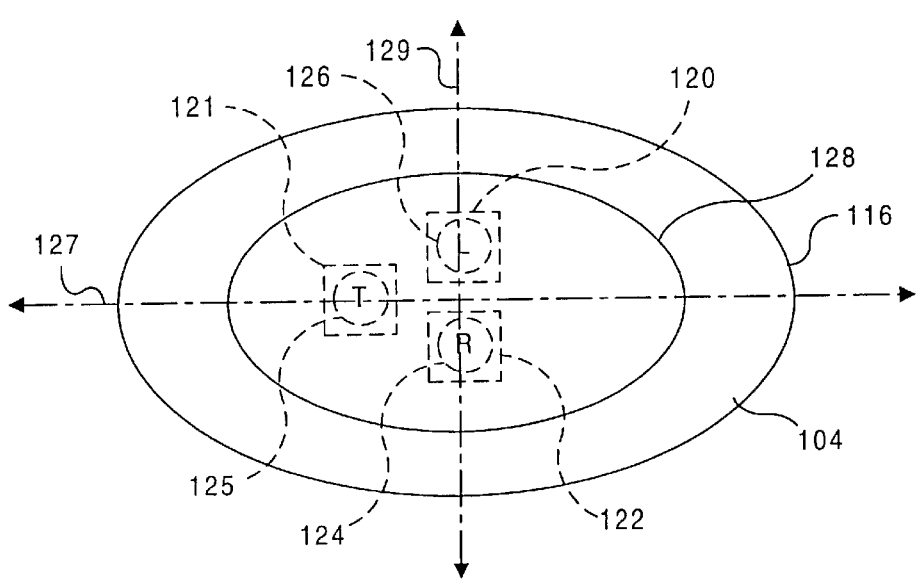
FIG. 4B is a bottom view of the external transmitter disposed over the internal receiver.

In FIG. 4B, a bottom view is portrayed of external transmitter 116 disposed over internal receiver 128. Left sensor 120 is coaxially aligned with left magnet 126, and similarly right sensor 122 is coaxially aligned with right magnet 124. The coaxially aligned magnets and sensors are disposed along aligned latitudinal axes 129 of external transmitter 116 and internal receiver 128. Moreover, Hall effect sensor 121 is coaxially aligned with magnet 125 and disposed along aligned longitudinal axes 127 of external transmitter 116 and internal receiver 128. While the signals produced by Hall effect sensors 120 and 122 can indicate when the latitudinal axes of the external transmitter and the internal receiver are aligned, the signal produced by optional Hall effect sensor 121 is required to determine whether external transmitter 116 is tilted about its latitudinal axes relative to internal receiver 128. In this way, the combination of the three pairs of sensors and magnets enables display 110 to fully indicate when external transmitter 116 is aligned relative to internal receiver 128 and indicates the distance separating the external transmitter and internal receiver.

As shown in FIG. 4A, an LED 131 will be illuminated at the top end of array 123 when the latitudinal and longitudinal axes of external transmitter 116 are aligned relative to the corresponding axes of internal receiver 128, i.e., when bottom surface 104 of external transmitter 116 and top surface 106 of internal receiver 128 are parallel along both the longitudinal and latitudinal axes and are separated by no more than the minimum anticipated distance. If the separation is greater than the minimum anticipated distance, an LED that is below the top of array 123 will be illuminated. Generally, the external transmitter will be aligned parallel with the internal receiver when the same corresponding LEDs are illuminated in array 123 as in the left and right portions of the display, since the LEDs that are illuminated when the external transmitter is directly above and aligned with the internal receiver depend upon the distance separating the two devices. However, when longitudinal axes 127 of external transmitter 116 and internal receiver 128 are not parallel, an LED will be illuminated in array 123 that does not correspond to the LEDs illuminated in left and right portions of the display. For example, if the second LED from the right end of left section 117 and the second LED from the left end of right section 119 are illuminated, the second LED from the top of array 123 should be illuminated to indicate that the external transmitter is parallel with the internal receiver.

The preferred embodiment thus employs the position of various illuminated LEDs 112 along the longitudinal axis of left section 117 and right section 119 of display 110 to indicate the position, distance between, and alignment of external transmitter 116 relative to internal receiver 128. However, it is envisioned that other types of displays could also be employed in the present invention. One type of display uses colored LEDs 112 that indicate the disposition of external transmitter 116 relative to internal receiver 128 by the color of the energized LED. The color of the illuminated LED corresponds to a specific disposition of external transmitter 116 relative to the location of internal receiver 128. As a further alternative, a computer monitor (not shown) could be employed to indicate the relative disposition of external transmitter 116, e.g., using graphic objects representing the internal receiver and the external transmitter and arranged to illustrate their relative disposition in three dimensions. Moreover, analog gages (or digital gages such as gage 133) and other types of visual displays can be used to indicate the position of external transmitter 116 relative to internal receiver 128.

Figure 5:
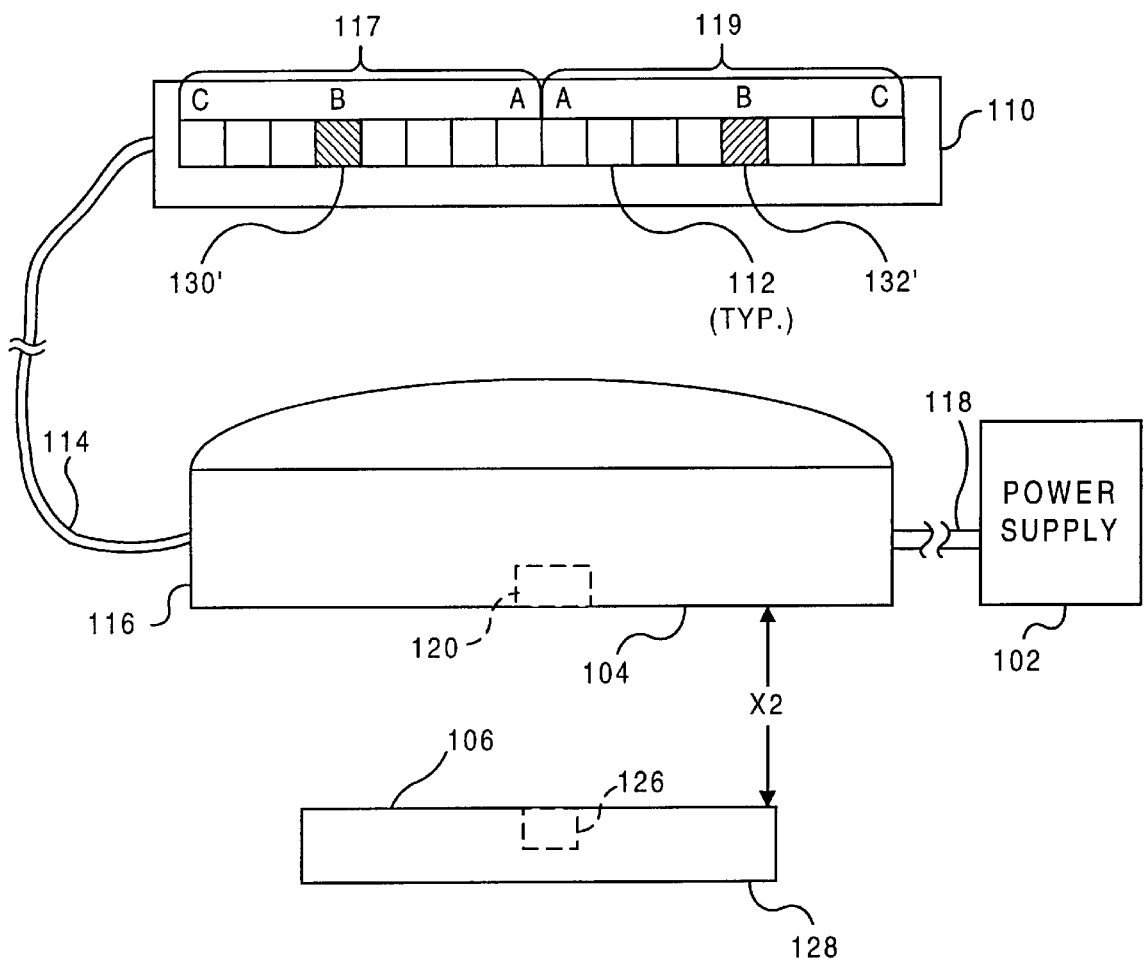
FIG. 5 is a side elevational view of the external transmitter disposed over the internal receiver, with an excessive distance separating the two, but only the LED portion of the display is shown to simplify the figure.

In FIG. 5, external transmitter 116 is shown disposed over internal receiver 128 and in proper alignment with the internal receiver. The bottom view of this arrangement of the external transmitter and internal receiver is thus identical to FIG. 4B. However, the separation distance (X2) between the external transmitter and the internal receiver in the example shown in FIG. 5 is substantially greater than the minimally anticipated distance X1. For this distance between the external transmitter and the internal receiver, an LED 130' in the middle (at B) of left section 117 of display 110 is illuminated, and in the middle of the right section of the display (also at B), an LED 132' is illuminated. If external transmitter 116 is tilted relative to internal receiver 128 or moved transversely or longitudinally relative to the internal receiver (but not closer to the internal receiver), LEDs that are further from the center of display 110 will be illuminated, but such movement will not cause LEDs that are closer to the center of the display to be illuminated. In this case, the illuminated LEDs in display 110 indicate to the user that external transmitter 116 is coaxially and longitudinally aligned with internal receiver 128 just as in the example of FIGS. 4A and 4B, but that the distance separating the external transmitter from the internal receiver is substantially greater than the minimally anticipated distance. For a selected resolution range, the user can refer to a table to determine the distance between the external transmitter and internal receiver that corresponds to LEDs 130' and 132' being illuminated. Alternatively, display 110 can include a scale of distances corresponding to each of the LEDs in the display, with an appropriate multiplier being applied depending upon the range selected by the user. In this case, the user can read the distance adjacent to the illuminated LED directly from the display when the LEDs that are illuminated in left section 117 and right section 119 are equidistant from the center, at the right end of the left section and the left end of the right section.

Figure 6A:
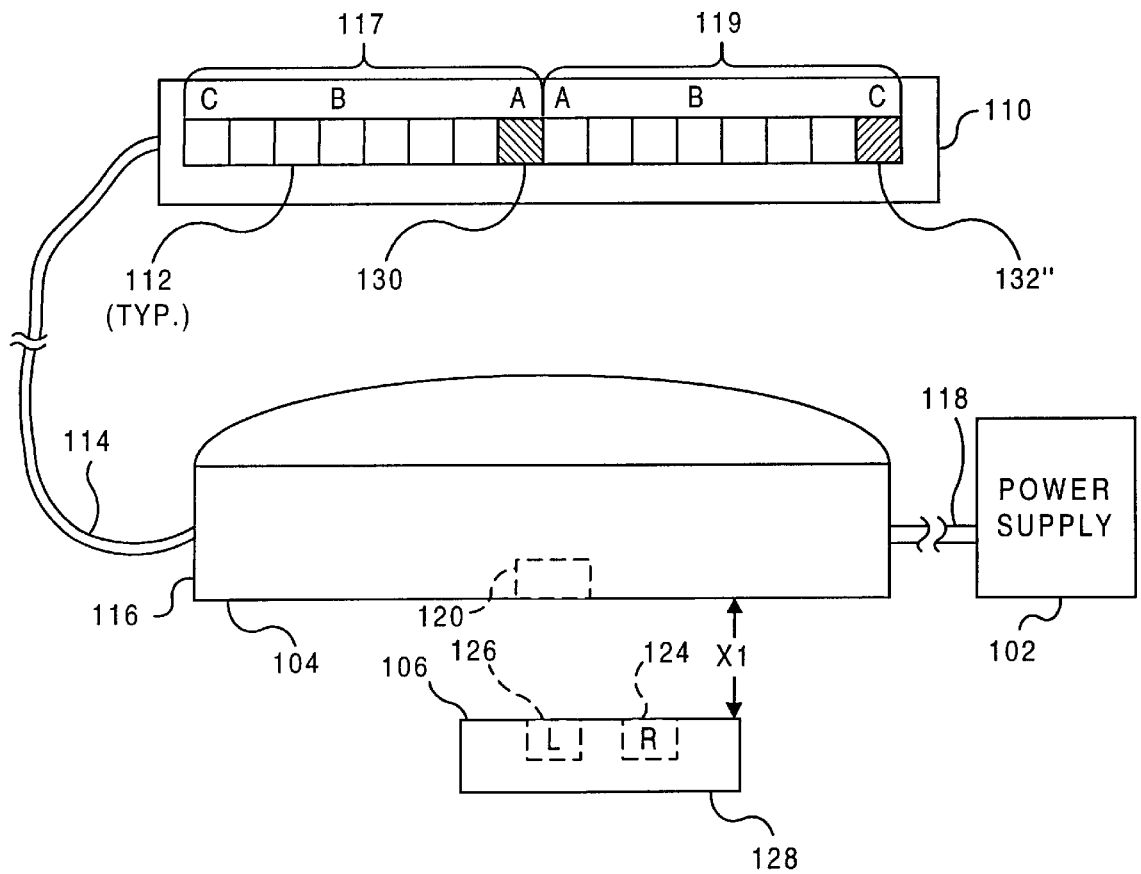
FIG. 6A is a side view of the external transmitter disposed over the internal receiver, with the longitudinal axis of the internal receiver oriented perpendicular to the longitudinal axis of the external transmitter, but only the LED portion of the display is shown to simplify the figure.
Figure 6B:
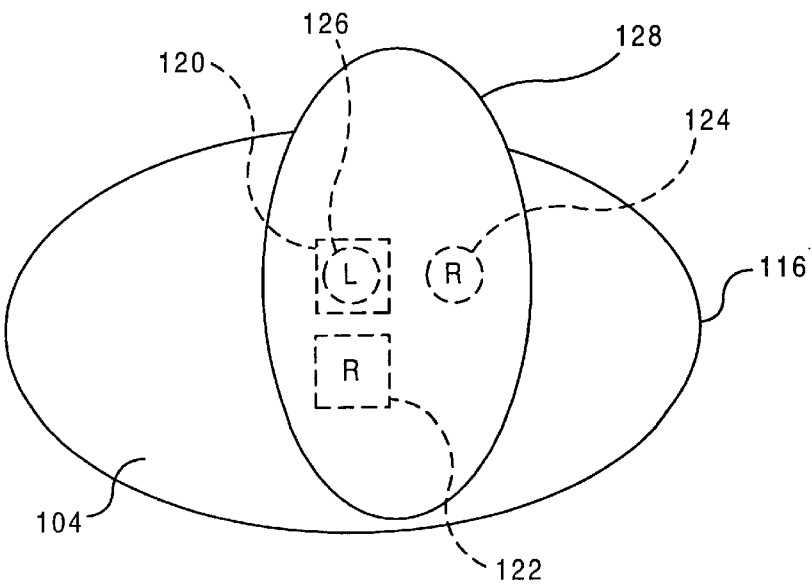
FIG. 6B is a bottom view of the external transmitter disposed over the internal receiver, with the longitudinal axis of the internal receiver oriented perpendicular to the longitudinal axis of the external transmitter.

FIG. 6A illustrates a side view of external transmitter 116 centrally disposed over internal receiver 128. In this example, the external transmitter is positioned at the minimally anticipated distance (X1) from the internal receiver, but the longitudinal axis of the external transmitter is substantially perpendicular to the internal receiver's longitudinal axis. LED 130 at the end of left section 117 closest to the center of display 110 is illuminated, and an LED 132" at the end of right section 119 that is farthest from the center of the display is illuminated. The illuminated LEDs in display 110 indicate to the user that Hall effect sensor 120 is aligned with permanent magnet 126 in internal receiver 128, but that Hall effect sensor 122 is not aligned with permanent magnet 124. The misalignment of these two devices is clearly shown in FIG. 6B.

In the example of FIG. 7A, external transmitter 116 is disposed over internal receiver 128 at the minimally anticipated distance (X1) and the longitudinal axes of the two devices are aligned; but, the latitudinal axis of the external transmitter is offset a distance (X3) from the latitudinal axis of the internal receiver. Hall effect sensors 120 and 122 are therefore not aligned with permanent magnets 126 and 124, respectively. An LED 130" disposed at the left end of left section 117 is illuminated, and an LED 132" disposed at the right end of right section 119 is illuminated in display 110. The disposition of the illuminated LEDs in the display indicates that external transmitter 116 is completely misaligned with internal receiver 128. FIG. 7B clearly shows the extent of the misalignment of the Hall effect sensors and the permanent magnets.

In FIG. 8, the present invention is used to enable external transmitter 116 to be properly aligned and positioned relative to internal receiver 128 so that electrical energy can be most efficiently transcutaneously transferred into a chest region (or abdominal region) 140 of a patient. External transmitter 116 is disposed against the epidermal surface of a skin layer 142 of the patient, and internal receiver 128 is positioned subcutaneously beneath the external transmitter. Hall effect sensor 120 is thus aligned with permanent magnet 126, and although not shown, Hall effect sensor 122 is aligned with permanent magnet 124. The illuminated LEDs 130 and 132 are disposed immediately adjacent to each other, on each side of the center of display 110. Their disposition indicates that external transmitter 116 and internal receiver 128 are in proper alignment and positioned at the minimally anticipated distance from each other.

It is contemplated that the present invention can also be used for aligning and positioning other types of external and internal devices that are separated by tissue, and the invention is not limited to applications involving energy or data transfer. Since the internal device will not be visible inside an organ or under the dermal layer of a patient's body, the present invention is clearly applicable to assist in orienting the external device relative to the internal device, regardless of the purpose of the devices. The present invention is also particularly well suited for determining the distance between external transmitter 116 and internal receiver 128 and can be employed in that regard for a non-medical use.

Furthermore, in the preferred embodiment, the poles of magnets 124 and 126 disposed on internal receiver 128 are oriented in the same direction, i.e., either with both north poles facing out or both south poles facing out. The disposition of the two poles in the same direction enables the present invention to determine when top surface 106 is flipped over, i.e., oriented 180° away from bottom surface 104 of internal receiver 128. Alternatively, the two poles of magnets 124 and 126 can be oriented in opposite directions to enable the present invention to determine if the internal receiver is rotated 180° about its center, i.e., end-for-end relative to a preferred rotational position. Additionally, it is contemplated that additional pairs of magnets and sensors may optionally be employed in the external transmitter and internal receiver to improve the resolution in determining the disposition of external transmitter 116 relative to internal receiver 128.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. Apparatus for determining a position of an external device relative to an implanted device that is separated from the external device by tissue, to enable said external device to be aligned with the implanted device, comprising:

(a) a magnet disposed on the external device;

(b) a magnetic field sensor disposed on the implanted device, said magnetic field sensor producing a signal indicative of a magnetic field strength; and (c) an indicator coupled to the magnetic field sensor to receive the signal, said indicator providing an indication of the position of the external device relative to the implanted device as a function of the magnetic field strength sensed by the magnetic field sensor as said external device is moved adjacent to the implanted device, such that the indicator alerts a user when said external device is aligned with said implanted device.

2. Apparatus for determining a position of an external device relative to an implanted device that is separated from the external device by tissue, to enable said external device to be aligned with the implanted device, comprising:

(a) a magnet disposed on one of the external device and the implanted device;

(b) a magnetic field sensor disposed on another of the external device and the implanted device, said magnetic field sensor producing a signal indicative of a magnetic field strength;

(c) an indicator coupled to the magnetic field sensor to receive the signal, said indicator providing an indication of the position of the external device relative to the implanted device as a function of the magnetic field strength sensed by the magnetic field sensor as said external device is moved adjacent to the implanted device, such that the indicator alerts a user when said external device is aligned with said implanted device;

(d) another magnet disposed on one of the external device and the implanted device;

(e) another magnetic field sensor disposed on another of the external device and the implanted device, said other magnetic field sensor producing another signal indicative of a magnetic field strength; and (f) another indicator coupled to the other magnetic field sensor to receive the other signal, said other indicator providing an indication of the position and orientation of the external device relative to the implanted device as a function of the magnetic field strength sensed by the other magnetic field sensor as said external device is moved adjacent to the implanted device.

3. The apparatus of claim 2, wherein the magnetic field sensor comprises one of a Hall effect sensor and a magneto resistive sensor.

4. The apparatus of claim 2, wherein the magnetic field sensors are disposed at spaced-apart locations on the external device.

5. The apparatus of claim 2, wherein the magnets are disposed at spaced-apart locations on the implanted device.

6. The apparatus of claim 2, wherein the indicator comprises a plurality of light sources and a driver circuit coupled to receive the signal, said driver circuit selectively energizing specific ones of the light sources as an indication of the field strength, and thus, of the position of the external device relative to the implanted device.

7. Apparatus for determining a position and alignment of an external device relative to an implanted device, to enable the external device to be aligned with the implanted device, said implanted device being separated from the external device by tissue, comprising:
   (a) two magnets disposed in the implanted device at spaced-apart locations;
   (b) two magnetic field sensors disposed in the external device at spaced-apart locations generally corresponding to the spaced-apart locations of the magnets in the implanted device, said magnetic sensors each producing an electrical signal indicative of magnetic field strength; and
   (c) an indicator coupled to receive the signals produced by the magnetic field sensors and in response thereto, producing an indication of the magnetic field produced by the magnets and thus of a position and orientation of the external device relative to the implanted device, said indication enabling the external device to be moved to a position opposite to and aligned with the implanted device.

8. The apparatus of claim 7, wherein the indicator comprises a plurality of light sources arranged in an array, at least one of said plurality of light sources being energized to indicate a relative alignment of one of the magnets with one of the magnetic field sensors, at least another of said plurality of light sources being energized to indicate a relative alignment of the other of the magnets with the other of the magnetic field sensors.

9. The apparatus of claim 7, wherein the plurality of light sources are arranged side by side, forming a first section and a second section, said at least one of the light sources that is energized being in said first section, and said at least another of said light sources that is energized being in said second section, a disposition of each of the light sources that are energized in said first and second sections indicating the relative magnetic field strengths.

10. The apparatus of claim 7, wherein the magnetic field sensors each comprises one of a Hall effect sensor and a magneto resistive sensor.

11. The apparatus of claim 7, wherein the magnets are oriented so that their poles are in opposite directions.

12. The apparatus of claim 7, wherein the magnets are oriented so that their poles are in the same directions.

13. The apparatus of claim 7, further comprising:
   (a) another magnet disposed in the implanted device at another location that is substantially spaced apart from a line through said two magnets;
   (b) another magnetic field sensor disposed on the external device at another location that is substantially spaced apart from a line through said two magnetic field sensors and generally corresponds to the location of the other magnet on the implanted device, the other magnetic sensor producing an electrical signal indicative of magnetic field strength; and
   (c) an indicator coupled to receive the signals produced by the other magnetic field sensor and in response thereto, producing an indication of the magnetic field produced by the other magnet and thus of a position and tilt of the external device relative to the implanted device, said indication enabling the external device to be moved to a position opposite to and aligned with the implanted device.

14. The apparatus of claim 7, wherein the indicator comprises an audible signal having at least two distinguishable characteristics, one characteristic varying with misalignment of one of the magnets relative to one of the magnetic field sensors, and another characteristic varying with misalignment of the other of the magnets relative to the other of the magnetic field sensors.

15. A method for determining a position of an external device in relation to an implanted device that is disposed within a patient's body and separated from the external device by tissue to enable the external device to be located in a desired position relative to the implanted device, comprising the steps of:
   (a) producing a magnetic field at a defined position on the external device;
   (b) sensing the magnetic field at a defined position on the implanted device, and in response thereto, producing a signal indicative of a strength of the magnetic field at the defined position on said external device; and
   (c) displaying an indication of the strength of the magnetic field sensed as the external device is moved relative to the implanted device, said indication enabling the external device to be located in the desired position relative to the implanted device.

16. A method for determining a position of an external device in relation to an implanted device that is disposed within a patient's body and separated from the external device by tissue to enable the external device to be located in a desired position relative to the implanted device, comprising the steps of:
   (a) producing a magnetic field at a defined position on one of the external device and the implanted device;
   (b) sensing the magnetic field at a defined position on the other of the external device and the implanted device, and in response thereto, producing a signal indicative of a strength of the magnetic field at the defined position on said other of the external device and the implanted device;
   (c) displaying an indication of the strength of the magnetic field sensed as the external device is moved relative to the implanted device, said indication enabling the external device to be located in the desired position relative to the implanted device;
   (d) producing another magnetic field at a different defined position on said one of the external device and the implanted device;
   (e) sensing the other magnetic field at a different defined position on said other of the external device and the implanted device and producing another signal indicative of the strength of the other magnetic field at the different defined position; and
   (f) providing an indication of a relative alignment and orientation of the external device and the implanted device as a function of the signal produced at each position on the other of the external device and implanted device as the external device is moved to the implanted device.

17. The method of claim 16, further providing a visual indication of the relative strength of the magnetic field using a plurality of light sources, at least one of which is selectively energized as a function of the signal.

18. The method of claim 16, further providing an audible indication of the relative strength of the magnetic field by varying a characteristic of an audible signal as a function of the signal.

19. The method of claim 16, further providing a visual indication of the relative strength of the magnetic field sensed at each position by energizing selected light sources in an array of light sources, a disposition of each light source that is energized indicating the relative strength of the magnetic field at each position where the magnetic field is sensed.

20. The method of claim 19, wherein the array of light sources is divided into two sections, a disposition of an energized light source in each section indicating the relative strength of the magnetic field at a different one of the positions where the magnetic field is sensed.

21. The method of claim 16, further providing colored light sources that are energized to provide a visual indication of the relative strength of the magnetic field at each location, and selecting a color of the light sources that are energized as a function of the signal at each position.

22. The method of claim 16, further providing a plurality of magnetic field sensors, each magnetic field sensor comprising one of a Hall sensor and a magneto resistive sensor, said plurality of magnetic field sensors being disposed at spaced-apart positions on the external device, and sensing the magnetic field with said plurality of magnetic field sensors.

23. The method of claim 16, wherein the magnetic field is produced at each position using permanent magnets that are disposed in spaced-apart positions on the implanted device.

24. The method of claim 16, further comprising the steps of:
(a) producing a magnetic field at a specified position on said one of the external device and the implanted device that is substantially spaced apart from a line through the defined positions at which the other magnetic fields are produced;
(b) sensing the magnetic field at a specified position on the other of the external device and the implanted device at a specified position that is substantially spaced apart from a line through the defined positions at which the other magnetic fields are sensed and generally corresponding to the specified position at which the magnetic field is produced; and
(c) displaying an indication of the strength of the magnetic field sensed at the specified position determinative of a tilt of the external device relative to the implanted device, said indication enabling the external device to be located in the desired position and in alignment with the implanted device.

25. The method of claim 16, further providing that the signals produced by sensing the magnetic field at each position indicate a distance separating the external device and the implanted device.

26. A method for determining a misalignment of an external transmitter relative to an implanted internal receiver that is separated from the external transmitter by a layer of tissue, comprising the steps of:
(a) producing a magnetic field at each of two disparate locations on the implanted internal receiver;
(b) sensing the magnetic field produced at each of the two disparate positions on the implanted internal receiver at two corresponding positions on the external transmitter and producing signals indicative of a strength of the magnetic field at each of the two corresponding positions; and
(c) in response to the signals at each of the two corresponding positions on the external transmitter, providing an indication of the orientation and the position of the external transmitter as it is moved about relative to the implanted internal receiver, thereby enabling the external transmitter to be positioned opposite to and aligned with the implanted internal receiver.

27. The method of claim 26, wherein the step of providing an indication comprises the step of providing two indicators that separately represent the relative magnetic field strength at the two positions on the external transmitter.

28. The method of claim 26, wherein the step of providing an indication comprises the step of providing a plurality of light sources arranged in an array having two sections, a selected light source in each section being energized to indicate the relative alignment of a different one of the two disparate locations on the implanted internal receiver with a different one of the two disparate positions on the external transmitter.

29. The method of claim 28, wherein a disposition of the light source that is energized in each section indicates the relative magnetic field strength at one of the disparate positions.

30. The method of claim 28, wherein a color of the light source that is energized in each section indicates the relative magnetic field strength at one of the disparate positions.

31. The method of claim 26, further providing two different characteristics of an audible signal to indicate the orientation and the position of the external transmitter as it is moved about relative to the implanted internal receiver, each characteristic being associated with a different one of the signals.

32. The method of claim 26, further comprising the step of providing an indication of a distance separating the external transmitter from the implanted internal receiver.

33. The method of claim 26, further comprising the steps of:
(a) producing a magnetic field at a third location on the implanted internal receiver, said third location being substantially spaced apart from a line through said two disparate locations on the implanted internal receiver;
(b) sensing the magnetic field produced at the third location on the implanted internal receiver at a third location on the external transmitter, said third location on the external transmitter being substantially spaced apart from a line through said two corresponding locations at which the magnetic fields are sensed, and producing a signal indicative of a strength of the magnetic field produced at the third location on the implanted internal receiver, said third location on the external transmitter corresponding to the third location on the implanted internal receiver; and
(c) in response to the signal produced by sensing the magnetic field at the third location on the external transmitter, providing an indication of tilt of the external transmitter relative to the implanted internal receiver, said indication in combination with the indication of the orientation and the position provided at each of the two corresponding positions on the external transmitter be used for aligning the external transmitter with the implanted internal receiver along orthogonal axes.

34. A method for determining an alignment between an external device and an implanted device, comprising the steps of:
(a) producing a magnetic field at a first position on one of the external device and the implanted device;
(b) sensing the magnetic field at a first position on the other of the external device and the implanted device, and in response thereto, producing a signal indicative of a strength of the magnetic field at the first position on said other of the external device and the implanted device;

(c) providing an indication of the strength of the magnetic field sensed at the first position on said other of the external device and the implanted device as a function of the signal and thereby, an indication of the distance between the external device and the implanted device;

(d) producing a magnetic field at a second position on said one of the external device and the implanted device, said second position being spaced apart from the first position;

(e) sensing the magnetic field at a second position on said other of the external device and the implanted device and producing a signal indicative thereof, said second position being spaced apart from the first position on said other of the external device and implanted device and corresponding to the second position on said one of the external device and implanted device; and (f) providing an indication of the alignment of the external device and the implanted device, and the distance between the external device and the implanted device as a function of the signals produced by sensing the magnetic field at said first and second positions on said other of the external device and the implanted device.

35. The method of claim 34, wherein the step of providing an indication comprises the step of displaying a visually perceptible indicator of the magnetic field sensed at the first position, said visually perceptible indicator changing to indicate a range of relative magnetic field strength sensed at the first position on said other of the external device and the implanted device relative to the distance between said external device and said implanted device.

36. Apparatus for determining a distance and an alignment between an external device and an implanted device, comprising:

(a) a first magnet disposed at a first position on one of the external device and the implanted device;

(b) a first magnetic field sensor disposed at a first position on the other of the external device and the implanted device, said first magnetic field sensor producing a signal indicative of a magnetic field strength;

(c) a first indicator coupled to the first magnetic field sensor, said first indicator producing a signal indicative of the strength of the magnetic field sensed by the first magnetic field sensor, said first indicator also indicating the distance between the external device and the implanted device as a function of said signal;

(d) a second magnet disposed on said one of the external device and the implanted device and spaced apart from the first magnet;

(e) a second magnetic field sensor disposed at a second position on the other of the external device and the implanted device and spaced apart from the first position disposed thereon, said second magnetic field sensor producing a signal indicative of a magnetic field strength sensed by the second magnetic field sensor; and (f) a second indicator coupled to the second magnetic field sensor, said second indicator producing a signal indicative of the strength of the magnetic field sensed by the second magnetic field sensor, and of the distance between the external device and the implanted device as a function of said signal produced by said second magnetic field sensor, said first and second indicators together indicating when the external device is aligned with the implanted device.

37. The apparatus of claim 36, wherein the first indicator is a visual indicator that includes a visual display indicative of a relative magnetic field strength and of the distance between the external device and the implanted device.

38. The apparatus of claim 36, wherein the first magnetic field sensor comprises one of a Hall effect sensor and a magneto resistive sensor.

39. Apparatus for transmitting energy from an external transmitter to an implanted receiver, by determining a position of the external transmitter relative to the implanted receiver, which is separated from the external transmitter by tissue, to enable said external transmitter to be aligned with the implanted receiver, to increase an efficiency with which the energy is transmitted, comprising:

(a) a magnet disposed on one of the external transmitter and the implanted receiver;

(b) a magnetic field sensor disposed on another of the external transmitter and the implanted receiver, said magnetic field sensor producing a signal indicative of a magnetic field strength; and (c) an indicator coupled to the magnetic field sensor to receive the signal, said indicator providing an indication of the position of the external transmitter relative to the implanted receiver as a function of the magnetic field strength sensed by the magnetic field sensor as said external transmitter is moved adjacent to the implanted receiver, so that said external transmitter can be aligned with said implanted receiver.

40. Apparatus for transmitting energy from an external transmitter to an implanted receiver, by determining a position of the external transmitter relative to the implanted receiver, which is separated from the external transmitter by tissue, and to enable said external transmitter to be aligned with the implanted receiver, in order to increase an efficiency with which the energy is transmitted, comprising:

(a) a magnet disposed on one of the external transmitter and the implanted receiver;

(b) a magnetic field sensor disposed on another of the external transmitter and the implanted receiver, said magnetic field sensor producing a signal indicative of a magnetic field strength;

(c) an indicator coupled to the magnetic field sensor to receive the signal, said indicator providing an indication of the position of the external transmitter relative to the implanted receiver as a function of the magnetic field strength sensed by the magnetic field sensor as said external transmitter is moved adjacent to the implanted receiver, so that said external transmitter can be aligned with said implanted receiver;

(d) another magnet disposed on said one of the external transmitter and the implanted receiver;

(e) another magnetic field sensor disposed on said other of the external transmitter and the implanted receiver, said other magnetic field sensor producing another signal indicative of a magnetic field strength; and (f) another indicator coupled to the other magnetic field sensor to receive the other signal, said other indicator providing an indication of the position and orientation of the external transmitter relative to the implanted receiver as a function of the magnetic field strength sensed by the other magnetic field sensor as said external transmitter is moved adjacent to the implanted receiver and thereby enabling the external transmitter to be aligned with the implanted receiver so as to most efficiently transfer energy to the implanted receiver from the external transmitter.

41. The apparatus of claim 40, wherein each of the magnetic field sensors comprises one of a Hall effect sensor and a magneto resistive sensor.

42. The apparatus of claim 40, wherein the magnetic field sensors are disposed at spaced-apart locations on the external transmitter.

43. The apparatus of claim 40, wherein the magnets are disposed at spaced-apart locations on the implanted receiver.

44. The apparatus of claim 40, wherein each of the indicators comprises a plurality of light sources and a driver circuit coupled to receive the signal, said driver circuit selectively energizing specific ones of the light sources as an indication of the field strength, and thus, of the position of the external transmitter relative to the implanted receiver.

45. A method for increasing the efficiency of the transcutaneous transmission of energy from an external transmitter to an implanted receiver, comprising the steps of:

(a) locating the external transmitter adjacent the implanted receiver by:
      (i) producing a magnetic field at a first position on one of the external device and the implanted receiver;
      (ii) sensing the magnetic field at a first position on another of the external transmitter and the implanted receiver, and in response thereto, producing a signal indicative of a strength of the magnetic field at the first position on said other of the external transmitter and the implanted receiver; and
      (iii) providing an indication of the strength of the magnetic field sensed at the first position on said other of the external transmitter and the implanted receiver as a function of the signal and thereby, an indication of the distance between the external transmitter and the implanted receiver;

(b) energizing the external transmitter for a length of time required to transfer a desired amount of energy to the implanted receiver;

(c) producing a magnetic field at a second position on said one of the external transmitter and the implanted receiver, said second position being spaced apart from the first position;

(d) sensing the magnetic field at a second position on said other of the external transmitter and the implanted receiver and producing a signal indicative thereof, said second position being spaced apart from the first position on said other of the external transmitter and implanted receiver and corresponding to the second position on said one of the external transmitter and implanted receiver; and (e) providing an indication of the alignment of the external transmitter and the implanted receiver, and the distance between the external transmitter and the implanted receiver as a function of the signals produced by sensing the magnetic field at said first and second positions on said other of the external transmitter and the implanted receiver.

46. The method of claim 45, wherein each of the steps of providing an indication comprises the step of displaying a visually perceptible indicator of the magnetic field sensed at one of the first position and the second position, said visually perceptible indicator indicating a range of relative magnetic field strength sensed at one of the first position and the second position on said other of the external transmitter and the implanted receiver relative to the distance between said external transmitter and said implanted receiver.

* * * * *